US005753226A

United States Patent [19]
Greene et al.

[11] Patent Number: 5,753,226
[45] Date of Patent: May 19, 1998

[54] METHODS OF ENHANCING EPITHELIAL CELL PROLIFERATION

[75] Inventors: Mark I. Greene, Penn Valley; George Cotsarelis, Berwyn, both of Pa.

[73] Assignee: The Trustees of the University of Pennsylvania, Philadelphia, Pa.

[21] Appl. No.: 419,903

[22] Filed: Apr. 11, 1995

[51] Int. Cl.$^6$ .................... A61K 39/395; A61K 38/02; A61K 38/03; A61K 39/15
[52] U.S. Cl. .................... 424/130.1; 424/133.1; 424/143.1; 424/152.1; 424/172.1; 514/2; 514/14; 514/15
[58] Field of Search .................... 424/130.1, 147.1, 424/186.1, 204.1, 215.1, 133.1, 143.1, 152.1, 172.1; 530/326, 327, 387.1, 388.3, 389.4, 826; 930/220, 260; 514/2, 14, 15

[56] References Cited

U.S. PATENT DOCUMENTS

5,334,702   8/1994   Greene et al. .................... 530/323

OTHER PUBLICATIONS

Barrandon, Y. and Green, "Cell Migration is Essential for Sustained Growth of Keratinocyte Colonies: the Roles of Transforming Growth Factor–α and Epidermal Growth Factor", *Cell* 1987, 50, 1131–1137.
Brown, G. et al., "Enhancement of Epidermal Regeneration by Biosynthetic Epidermal Growth Factor", *J. Exp. Med.* 1986, 163, 1319–1324.
Cellini, M. et al., "Epidermal Growth–Factor in the Topical Treatment of Herpetic Corneal Ulcers", *Ophthalmologica* 1994, 208, 37–40.
Falanga, V., "Growth Factors and Wound Healing", *Dermatologic Clinics* 1993, 11, 667–675.
Grando, S.A. et al., "Computerized Microassay of Keratinocyte Cell–Plastic Attachment and Proliferation for Assessing Net Stimulatory, Inhibitory and Toxic Effects of Compounds on Nonimmortalized Cell–Lines", *Skin Pharmacology* 1993, 6, 135–147.
Jaworsky, C. et al., "Characterization of Inflammatory Infiltrates in Male Pattern Alopecia; Implications for Pathogenesis", *British J. of Dermatology* 1992, 127, 239–246.
McMurray, J. and Lewis, "The Synthesis of Cyclic Peptides Using Fmoc Solid–Phase Chemistry and the Linkage Gent 4–(4–Hydroxymethyl–3–methoxyphenoxy)–butyric Acid", *Tetrahedron Letters* 1993, 34(50), 8059–8062.
McMurray, J. et al., "Cyclic Peptide Substrates of pp60$^{c-src}$ Synthesis and Evaluation", *Int. J. Peptide Protein Res.* 1993, 42, 209–215.
Merrifield, R.B., "Solid Phase Peptide Synthesis. I. The Synthesis of a Tetrapeptide", *J. Am. Chem. Soc.* 1963, 85, 2149–2154.
Pfister, R., "The Alkali Burned Cornea. I. Epithelial and Stromal Repair", *Exp. Eye Res.* 1976, 23, 519–535.
Sawaya, M.E., "Biochemical Mechanisms Regulating Human Hair Growth", *Skin Pharmacology* 1994, 7, 5–7.

Scardovi, C. et al., "Epidermal Growth–Factor in the Topical Treatment of Traumatic Corneal Ulcers", *Ophthalmologica* 1993, 206, 119–124.
Schultz, G. et al., "Effects of Growth Factors on Corneal Wound Healing", *Acta Ophthalmol. Suppl.* 1992, 60–66.
Wood, S. and Wetzel, "Novel Cyclization Chemistry Especially Suited for Biologically Derived, Unprotected Peptides", *Int. J. Peptide Protein Res.* 1992, 39, 533–.
Bhora, et al., "Effect of Growth Factors on Cell Proliferation and Epithelialization in Human Skin", *J. Surg. Res.*, 1995, 59, 236–244.
Cohen, et al., "Anti–reovirus receptor antibody accelerate expression of the optic nerve oligodendrocyte developmental program", *Proc. Natl. Acad. Sci. USA*, 1991, 88, 1266–1270.
Danilenko, et al., "Growth Factor in Porcine Full and Partial Thickness Burn Repair", *Am. J. Pathol.*, 1995, 147(5), 1261–1277.
Garlick, et al., "Effect of TGF–β1 on Re–Epithelialization of Human Keratinocytes In Vitro: An Organotypic Model", *TGF–β1 Re–Epithelialization*, 1994, 103(4), 554–559.
Williams et al., "Contact residues and predicted structure of the reovirus type3–receptor interaction", *J. Biol. Chem.*, 266(14), pp. 9241–9250, May 1991.
Williams et al., "Development of Biologically Active Peptides Based on Antibody Structure", *Proc Natl Acad Sci U S A* 86(14), 5537–5541, 1989.
Alberts et al., Molecular Biology of the Cell, Garland, New York, pp. 942–943, 1983.
Saragovi et al., "A receptor that subserves reovirus binding can inhibit lymphocyte proliferation triggered by mitogenic signals", *DNA Cell. Biol.* 14, 653–664, Aug. 1995.
Bruck et al., "Nucleic–Acid Sequence of an Internal Image–Bearing Monoclonal Anti–Idiotype and its Comparison to the Sequence of the External Antigen", *Proc Natl Acad Sci U S A* 83 (17) 6578–6582, 1985.
Saragovi et al., "Design and Synthesis of a Mimetic from an Antibody Complementarity–Determining Region", *Science* 253, 792–795, 1991.

*Primary Examiner*—Marian C. Knode
*Assistant Examiner*—Donna C. Wortman
*Attorney, Agent, or Firm*—Pennie & Edmonds LLP

[57] ABSTRACT

Methods of enhancing epithelial cell proliferation are disclosed. The methods comprise the step of contacting epithelial cells with a compound that binds to reovirus type 3 receptor. Methods of treating an individual susceptible to or suffering from a condition, disease or disorder characterized by insufficient proliferation of epithelial cells are disclosed. The methods comprise the steps of identifying such individuals and administering to them a therapeutically effect amount of compound that binds to reovirus type 3 receptor and thereby enhances proliferation of epithelial cells. Methods of treating individuals suffering from wounds that involve epithelial cells are disclosed. The methods comprise the steps of identifying such individuals and administering to them a therapeutically effect amount of compound that binds to reovirus type 3 receptor and thereby enhances proliferation of epithelial cells.

46 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Phe  Lys  Thr  Asn  Lys
1                    5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Phe Asn Lys Leu
1
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Tyr Ser Gly Ser Thr
1               5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Ile Tyr Ser Gly Ser Thr
1               5
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: both ( i i ) MOLECULE TYPE: peptide ( x i ) SEQUENCE DESCRIPTION: SEQ ID NO:5:

```
Phe Lys Thr Asn Lys Cys Ile Tyr Ser Gly Ser Thr Cys Gln Phe
1               5                   10                  15
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: both ( i i ) MOLECULE TYPE: peptide ( x i ) SEQUENCE DESCRIPTION: SEQ ID NO:6:

```
Phe Lys Cys Ile Tyr Ser Gly Ser Thr Cys Gln Phe
1               5                   10
```

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( D ) TOPOLOGY: both ( i i ) MOLECULE TYPE: peptide ( x i ) SEQUENCE DESCRIPTION: SEQ ID NO:7:

```
Phe Asn Lys Leu Cys Ile Tyr Ser Gly Ser Thr Cys Gln Phe
1               5                   10
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: both ( i i ) MOLECULE TYPE: peptide ( x i ) SEQUENCE DESCRIPTION: SEQ ID NO:8:

```
Phe Lys Thr Asn Lys Cys Ile Tyr Ser Gly Ser Thr Cys Gln Phe
1               5                   10                  15
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: both ( i i ) MOLECULE TYPE: peptide ( x i ) SEQUENCE DESCRIPTION: SEQ ID NO:9:

```
Phe Cys Ile Tyr Ser Gly Ser Thr Cys Phe
1               5                   10
```

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( D ) TOPOLOGY: both ( i i ) MOLECULE TYPE: peptide ( x i ) SEQUENCE DESCRIPTION: SEQ ID NO:10:

```
Phe Cys Ile Tyr Ser Gly Ser Thr Cys Tyr
1               5                   10
```

METHODS OF ENHANCING EPITHELIAL CELL PROLIFERATION

FIELD OF THE INVENTION

The invention relates to methods of enhancing epithelial cell proliferation by administering specific compounds, antibodies, proteins or peptides. In particular, the invention relates to methods of enhancing proliferation of hair cells, skin cells and ocular cells.

BACKGROUND OF THE INVENTION

Epithelial cells make up the epithelium, a purely cellular layer which covers free surfaces including cutaneous, mucous, and serous. Examples of epithelial cells include the cells which are involved in hair growth, skin and eye cells. Proliferating epithelial cells include those cells involved in reepithelialization at sites of wounds during wound healing, skin grafts, and skin disorders characterized by aberrant proliferation.

Alopecia or hair loss can be categorized into scarring and nonscarring types. In nonscarring alopecia the stem cells responsible for continued renewal of the hair follicle are intact, therefore the potential for regrowth of the hair is always present. This type of hair loss includes early androgenetic alopecia (common baldness), alopecia areata and telogen effluvium (which may be caused by medications, hormonal abnormalities, pregnancy or stress).

Androgenetic alopecia occurs in both men and women. The affected hair follicles gradually become "miniaturized." Normally as each follicle progresses from a resting (telogen) state, typically lasting several months on the human scalp, back to a growing (anagen) state the entire lower follicle regenerates from a small collection of stem cells located in the midportion of the outer root sheath of the hair follicle. A proliferative burst of these cells marks the beginning of the new growing phase. In androgenetic alopecia, the regenerated follicle is smaller than its predecessor. This may be secondary to inadequate proliferation of the follicular stem cells secondary to either an inflammatory infiltrate (Jaworsky, C. et al. 1992 *Brit. J. Dermatol.* 127:239–246) or antiproliferative effects of testosterone (Sawaya, M. E. 1994) *Skin Pharmacolog.* 7:5–7).

Alopecia areata is an autoimmune disorder resulting in partial or complete loss of scalp and body hair. All age groups are affected, but children tend to have more extensive, less responsive hair loss. The condition may last for months or may go on for years. The recurrence rate approaches 100%. About 1–5% of all visits to a dermatologist are for alopecia areata. Often associated with thyroid disease, vitiligo, eczema or rarely pernicious anemia or collagen vascular disease, alopecia areata may cause profound psychological morbidity. The rapidly dividing matrix cells which normally produce a new hair are injured causing the hair follicle to stop proliferating and enter an early telogen or resting phase. This injury results from infiltration of the hair follicle predominantly by T-cell lymphocytes, and is considered an autoimmune disease. Similarly, hair loss resulting from collagen vascular disease (e.g. systemic or discoid lupus erythematosus) results from damage to the hair follicle by autoreactive T-cells.

Normally 5 to 10% of scalp hair follicles are in a resting or telogen state. These hairs are lost or "shed" on a daily basis. Telogen effluvium refers to increased shedding of hairs caused by an increase in the percentage of telogen hair follicles. This phenomenon is extremely common and may occur secondary to medications, hormonal abnormalities, febrile illness, pregnancy, stress or other factors. Usually the condition is transient lasting 2 to 6 months, however many people are susceptible to repeated bouts which may lead to chronic shedding and eventual thinning of the scalp hair.

Wound healing occurs through a complex series of events which can be divided into three phases: inflammatory, proliferative and remodeling. The timing of these phases overlaps. One of the earliest events necessary for wound healing in the skin and eye is epithelial proliferation which is required for reepithelialization.

Cutaneous ulcers or wounds may be caused by numerous conditions including vascular disease (arterial, venous or lymphatic), metabolic disorders (diabetes, necrobiosis lipoidica diabeticorum, porphyria cutanea tarda, gout, pancreatitis), infections (bacterial, viral, fungal), vasculitis (polyarteritis, systemic lupus, rheumatoid, Wegener's granulomatosis, drug-induced), drug side effects (ergotism, halogenodermas, anticoagulant induced necrosis) hematologic abnormalities (hypercoagulable states, sickle cell anemia, thalassemia, polycythemia vera, leukemia, dysproteinemia), tumors (primary cutaneous, metastatic to skin, Kaposi's sarcoma), pyoderma gangrenosum, trauma, burns, pressure sores, neuropathies, insect bites, lichen planus, bullous diseases, and Sweet's syndrome.

Skin grafting procedures create surgical wounds. Both the donor and recipient sites need to heal. The time required for reepithelialization presents a risk of infection and subsequent failure of the surgical procedure. An intact epithelium acts as a barrier to the environment and prevents infection. Any type of surgical procedure which disrupts the skin or eye must heal quickly in order to reduce risks of infection.

Skin disorders characterized by decreased or aberrant proliferation of the epithelium include photoaging, ulcerations, chronic wounds, steroid atrophy, scleroderma, actinic keratoses, ichthyoses, and seborrheic keratoses. Aberrant proliferation also occurs in hyperproliferative disorders caused by T-cell proliferation such as psoriasis and cutaneous T-cell lymphoma. In addition to effects on epithelial cell proliferation in treating psoriasis and cutaneous T-cell lymphoma, the compounds of the invention also block T-cell activation.

In addition to the skin, epithelial cells make up the ocular tissue. When epithelial cells of the eye are damaged such as in cases of ocular wounds. The epithelium normally regrows over an abraded cornea in a relatively rapid and predictable manner (Pfister, R. R. 1976 *Exp. Eye Res.* 23:519–535). However, numerous conditions or events may interfere with normal healing, and result in a persistent corneal epithelial defect. Herpes keratitis, collagen vascular disease, Sjögren's syndrome, tear film abnormalities, deinnervation and trauma including alkali burns may all cause a non-healing corneal epithelial defect to form.

Corneal transplants and corneal surgery are examples of situations where reepithelialization of ocular tissue is required. In most cases, corneal reepithelialization following corneal transplant or corneal surgery occurs relatively rapidly. The risk of infection following "routine" corneal transplants and surgeries is small but finite. During reepithelialization of the wound, there is a chance for infection and subsequent failure of the surgical procedure. The risk of surgical failure is especially high in "high risk" surgery such as corneal transplants for treatment of alkali-burned corneas. Presumably this is due to the neovascularization which develops in the cornea following alkali burns or other trauma.

Molecules that affect proliferative activity of epidermal cells include epidermal growth factor (EGF), transforming growth factor beta (TGFO), keratinocyte growth factor, Insulin-like growth I (IGF-I), Fibroblast growth factor (FGF) and cytokines such as interleukin 1 and interleukin 8. These substances are polypeptides which bind to cell surface receptors and which are normally found in the skin and eye. The genes encoding their production have been cloned and sequenced, and thus they are available in recombinant forms.

Recombinant human EGF has concentration-dependent in vitro and in vivo effects on epidermal and corneal epithelial cells. Recombinant human EGF has been used in animal studies and in clinical studies to promote epithelial proliferation and wound healing in the skin and eye. Peptide growth factors mitogenic for epithelial cells have demonstrated efficacy in accelerating the closure of split and full thickness wounds of the skin and cornea (for review see: Falanga, V. 1993 *Dermatolog. Clinics* 11:667–675, Schultz, G. et al. *Acta Ophthalmol. Suppl.* 1992, 60–62). EGF has also been used for the treatment of venous leg ulcers with limited success. EGF has also demonstrated efficacy in the treatment of herpetic corneal ulcers (Cellini, M. et al. 1994 Ophthalmologica 0208:37–40) and traumatic corneal ulcers (Scardovi, C. et al. 1993 *Ophthalmologica* 0206:119–124).

The mitogenic effects of EGF on epithelial cells in culture are well known (Barrandon, Y. and H. Green 1987 *Cell* 50:1131–1137). Most studies on the effects of EGF on wound healing have demonstrated enhanced regeneration of epithelium in both corneal and skin models (Brown, G. L. C. et al. 1986 *J. Exp. Med.* 1631319–1324). However, the inherent instability of polypeptides resulting in their rapid degradation by enzymes present in a wound is a major problem confronting the successful use of EGF or any recombinant growth factors in clinical situations.

There is a need for compounds and methods which enhance proliferation of epithelial cells. There is a need for compounds and methods which enhance proliferation of epithelial cells in the scalp. There is a need for compounds and methods for treating individuals suffering from or susceptible to alopecia including androgenetic alopecia, alopecia areata and telogen effluvium. There is a need for compositions and methods for treating individuals suffering from or susceptible to cutaneous ulcers, wounds, photoaging, ulcerations, chronic wounds, steroid atrophy, and scleroderma as well as hylierproliferative disorders such as psoriasis, ichthyosis, cutaneous T-cell lymphoma, actinic keratoses and seborrheic keratoses. There is a need for compositions and methods for reducing the risks of infection and rejection in individuals undergoing skin grafting procedures. There is a need for compositions and methods of treating individuals suffering from ocular wounds and ocular disorder such as herpes keratitis, collagen vascular disease, Sjorgen's syndrome, tear film abnormalities, deinnervation and trauma including alkali burns. There is a need for compositions and methods for reducing the risks of infection and rejection in individuals undergoing corneal transplants and corneal surgery.

SUMMARY OF THE INVENTION

The present invention relates to methods of enhancing epithelial cell proliferation. The methods comprise the step of contacting epithelial cells with a compound that binds to reovirus type 3 receptor. The compound is selected from the group consisting of isolated antibodies that bind to reovirus type 3 receptor, isolated reovirus hemagglutinin sigma 1 protein or a fragment thereof that binds to reovirus type 3 receptor, peptides that bind to reovirus type 3 receptor or peptide mimetics that bind to reovirus type 3 receptor.

The present invention provides peptides which are useful in methods of enhancing epithelial cell proliferation. Some peptides useful in methods of the invention have the formula:

$$R_1\text{-}R_2\text{-}R_3\text{-}R_4\text{-}R_5\text{-}R_6\text{-}R_7$$

wherein:

$R_1$ is 1–6 amino acid residues and at least one of which is tyrosine or phenylalanine;

$R_2$ is a linking moiety which bonds with $R_1$, $R_3$ and $R_6$ such that a portion of the molecule is cyclicized;

$R_3$ is 0–13 amino acids;

$R_4$ is 4–6 amino acids;

$R_5$ is 0–13 amino acids;

$R_6$ is a linking moiety which bonds with $R_5$, $R_7$ and $R_2$ such that a portion of the molecule is cyclicized;

$R_7$ is 1–6 amino acid residues and at least one of which is tyrosine or phenylalanine;

wherein: $R_1$, $R_2$, $R_3$, $R_4$, $R_5$, $R_6$ and $R_7$ taken together are made up of 30 amino acids or less;

and $R_4$ is has either the formula:

$$\text{Tyr-Ser-}R_{41}\text{-Ser-Thr}$$

wherein $R_{41}$ is Gly, Pro or a flexible moiety which bonds to Ser and Ser and allow them to retain the psi/phi adjustment that occurs when $R_{41}$ is Gly; or the formula:

$$R_{42}\text{-Tyr-Ser-}R_{41}\text{-Ser-Thr}$$

wherein $R_{41}$ is Gly, Pro or a flexible moiety which bonds to Ser and Ser can be formed and allow them to retain the psi/phi adjustment that occurs when $R_{41}$ is Gly, and $R_{42}$ is Ile, Leu, Val, Gly or Met.

The present invention relates to methods of treating individuals who are susceptible to or who suffering from a condition, disease or disorder characterized by insufficient epithelial cell proliferation. The methods comprise the steps of identifying such individuals and administering to them, a therapeutically effect amount of compound which enhances proliferation of epithelial cells. The compound is selected from the group consisting of isolated antibodies that bind to reovirus type 3 receptor, isolated reovirus hemagglutinin sigma 1 protein or a fragment thereof that binds to reovirus type 3 receptor, peptides that bind to reovirus type 3 receptor or peptide mimetics that bind to reovirus type 3 receptor. Peptides used in the methods of the invention may have the formula:

$$R_1\text{-}R_2\text{-}R_3\text{-}R_4\text{-}R_5\text{-}R_6\text{-}R_7$$

wherein:

$R_1$ is 1–6 amino acid residues and at least one of which is tyrosine or phenylalanine;

$R_2$ is a linking moiety which bonds with $R_1$, $R_3$ and $R_6$ such that a portion of the molecule is cyclicized;

$R_3$ is 0–13 amino acids;

$R_4$ is 4–6 amino acids;

$R_5$ is 0–13 amino acids;

$R_6$ is a linking moiety which bonds with $R_5$, $R_7$ and $R_2$ such that a portion of the molecule is cyclicized; $R_7$ is 1–6 amino acid residues and at least one of which is tyrosine or phenylalanine;

wherein: $R_1$, $R_2$, $R_3$, $R_4$, $R_5$, $R_6$ and $R_7$ taken together are made up of 30 amino acids or less;
and $R_4$ is has either the formula:

Tyr-Ser-$R_{41}$-Ser-Thr wherein $R_{41}$ is Gly, Pro or a flexible moiety which bonds to Ser and Ser and allow them to retain the psi/phi adjustment that occurs when $R_{41}$ is Gly; or the formula:

$R_{42}$-Tyr-Ser-$R_{41}$-Ser-Thr wherein $R_{41}$ is Gly, Pro or a flexible moiety which bonds to Ser and Ser can be formed and allow them to retain the psi/phi adjustment that occurs when $R_{41}$ is Gly, and $R_{42}$ is Ile, Leu, Val, Gly or Met.

The present invention relates to methods of treating individuals who are suffering from wound that involve epithelial cells. The wounds may be the result of injuries, diseases, disorders, conditions, infections or brought about as the result of surgical procedures including surgical incisions or transplantation of tissue which includes and/or is in contact with epithelial cells. The methods comprise the steps of identifying individuals who are suffering from wound that involve epithelial cells and administering to them a therapeutically effect amount of compound which enhances proliferation of epithelial cells. The compound is selected from the group consisting of isolated antibodies that bind to reovirus type 3 receptor, isolated reovirus hemagglutinin sigma 1 protein or a fragment thereof that binds to reovirus type 3 receptor, peptides that bind to reovirus type 3 receptor or peptide mimetics that bind to reovirus type 3 receptor. Peptides used in the methods of the invention may have the formula:

$R_1$-$R_2$-$R_3$-$R_4$-$R_5$-$R_6$-$R_7$ wherein:

$R_1$ is 1–6 amino acid residues and at least one of which is tyrosine or phenylalanine;

$R_2$ is a linking moiety which bonds with $R_1$, $R_3$ and $R_6$ such that a portion of the molecule is cyclicized;

$R_3$ is 0–13 amino acids;

$R_4$ is 4–6 amino acids;

$R_5$ is 0–13 amino acids;

$R_6$ is a linking moiety which bonds with $R_5$, $R_7$ and $R_2$ such that a portion of the molecule is cyclicized;

$R_7$ is 1–6 amino acid residues and at least one of which is tyrosine or phenylalanine;

wherein: $R_1$, $R_2$, $R_3$, $R_4$, $R_5$, $R_6$ and $R_7$ taken together are made up of 30 amino acids or less;
and $R_4$ is has either the formula:

Tyr-Ser-$R_{41}$-Ser-Thr wherein $R_{41}$ is Gly, Pro or a flexible moiety which bonds to Ser and Ser and allow them to retain the psi/phi adjustment that occurs when $R_{41}$ is Gly; or the formula:

$R_{42}$-Tyr-Ser-$R_{41}$-Ser-Thr wherein $R_{41}$ is Gly, Pro or a flexible moiety which bonds to Ser and Ser can be formed and allow them to retain the psi/phi adjustment that occurs when $R_{41}$ is Gly, and $R_{42}$ is Ile, Leu, Val, Gly or Met.

DETAILED DESCRIPTION OF THE INVENTION

As used herein, the term "compound" is meant to refer to a protein, an antibody, a peptide or a peptide mimetic which is useful in the method of enhancing the proliferation of epithelial cells which is the method of the invention.

As used herein, the term "antibody" is meant to refer to complete, intact antibodies including monoclonal antibodies, chimeric antibodies and humanized antibodies as well as Fab and F(ab)$_2$ fragments of monoclonal antibodies, chimeric antibodies and humanized antibodies.

As used herein, the term "therapeutically effective amount" is meant to refer to an amount of a compound which produces a medicinal effect observed as an alleviation, elimination or reduction the severity of the disease, condition, disorder or injury or the symptoms thereof when it is administered to an individual who is susceptible to or suffering from such a disease, condition, disorder or injury. Therapeutically effective amounts are typically determined by the effect they have compared to the effect observed when a composition which includes no active ingredient is administered to a similarly situated individual.

The present invention relates to methods of enhancing epithelial cell proliferation comprising the step of contacting epithelial cells with a compound which binds to the reovirus hemagglutinin 1 sigma cellular receptor. According to the present invention, individuals suffering from conditions associated with epithelial cell growth as well as individuals undergoing surgical procedures involving epithelial cells can be treated with compounds to enhance proliferation of epithelial cells and thereby reduce the severity of the condition and/or facilitate recovery of damaged tissue.

It has been discovered that such compounds enhance proliferation of epithelial cells. The discovery that such compounds enhance proliferation of epithelial cells is particularly surprising in view of the reported observation that related antibodies and peptides inhibit T cell and fibroblast proliferation.

This surprising and unexpected biological activity makes such compounds useful as pharmacological agents in many applications and many methods.

In some embodiments, the methods of the present invention are useful to treat individuals identified as being susceptible to or suspected of suffering from diseases, conditions or disorders characterized by reduced or suppressed epithelial cell proliferation.

In some embodiments, the methods of the present invention are useful to treat individuals identified as being susceptible to or suspected of suffering from diseases, conditions or disorders in which symptoms are alleviated when epithelial cell proliferation is enhanced.

In some embodiments, the methods of the present invention are useful to treat individuals suffering from burns, wounds and ulcers to tissues comprising epithelial cells such as ocular burns, wounds and ulcers; oral burns, wounds and ulcers; rectal burns, wounds and ulcers; vaginal burns, wounds and ulcers; pulmonary burns, wounds and ulcers; sinus cavity burns, wounds and ulcers; and otic burns, wounds and ulcers.

In some embodiments, the methods of the present invention are useful to treat individuals undergoing surgical procedures for healing the tissue at the site of incision or in transplantation procedures involving epithelial cells such as skin grafts and corneal transplants.

The invention is particularly useful in treating individuals susceptible to or suffering from of various alopecia conditions associated with hair loss such as androgenetic alopecia, alopecia areata and telogen effluvium.

The invention is particularly useful in treating individuals suffering from burns, wounds and ulcers of tissue that includes epithelial cells, particularly the skin and eyes. Examples of eye injuries and conditions in which the invention is particularly useful include circumstances wherein the individual suffering from an eye injury or condition which results in corneal damage also suffers from conditions or events may interfere with normal healing, and result in a persistent corneal epithelial defect such as herpes keratitis, collagen vascular disease, Sjögren's syndrome, tear film abnormalities, deinnervation and trauma including alkali burns.

The invention is useful to facilitate healing of incision wounds from surgery, skin grafts and corneal transplants.

The invention is useful to treat individuals suffering from aphthae such as mouth and/or vaginal ulcers.

Compounds useful in the methods of the invention include those which bind to/interact with the type 3 reovirus receptor, i.e. the cellular receptor to which the reovirus viral cell attachment protein sigma 1 (the viral hemagglutinin) binds. Reovirus hemagglutinin sigma 1 protein binds to this protein during the reovirus infection process. Compounds that are useful in the methods that are the present invention include antibodies, proteins, peptides and peptide mimetics that each bind to the type 3 reovirus receptor.

Antibodies specific for the type 3 reovirus receptor that have been and/or can routinely be made include monoclonal antibodies, chimeric antibodies and humanized antibodies as well as Fab and F(ab)$_2$ fragments. Antibodies which bind specifically to human type 3 reovirus receptor may be produced by those having ordinary skill in the art using standard techniques and readily available starting materials. The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) ANTIBODIES: A Laboratory Manual, Cold Spring Harbor Laboratory, Cold Spring Harbor, N.Y.

Proteins useful in the methods of the present invention include reovirus hemagglutinin sigma 1 protein and derivatives thereof. Derivatives include proteins which comprise the amino acid sequence of reovirus hemagglutinin sigma 1 protein which interacts with the type 3 reovirus receptor or comprise the amino acid sequence of reovirus hemagglutinin sigma 1 protein including conservative substitutions, and deletions and insertion. Derivatives are characterized by there ability to interact with the type 3 reovirus receptor present on cells.

Some peptides useful in the methods of the present invention are peptides which consist of or comprise fragments of reovirus hemagglutinin sigma 1 protein and which bind to reovirus hemagglutinin sigma 1 receptor can be used in the methods of the invention. Those having ordinary skill in the art can identify fragments of reovirus hemagglutinin sigma 1. Peptides have been designed upon or derived from sequence information of the reovirus hemagglutinin 1 sigma protein. Specific sequences from the reovirus protein have been identified as corresponding to sequences of the variable region of biologically active anti-idiotypic antibodies raised against antibodies that bind to reovirus or biologically active anti-receptor antibodies that bind to the cellular receptor that reovirus attaches to prior to infection. Synthetic peptides have been constructed using the amino acid sequence information showing the corresponding sequences from the reovirus protein and the sequence of the variable region of the anti-idiotypic antibody or the variable region of the anti-receptor antibody. Techniques for deriving this information are found in related patent applications U.S. Ser. No. 07/940,654 filed Sep. 3, 1992, U.S. Ser. No. 702,833 filed May 20, 1991, U.S. Ser. No. 326,328 filed Mar. 21, 1989, U.S. Ser. No. 074,264 filed Jul. 16, 1987, U.S. Ser. No. 462,542 filed Jan. 9, 1990, U.S. Ser. No. 074,264 filed Jul. 16, 1987, U.S. Ser. No. 648,303 filed Jan. 25, 1991, U.S. Ser. No. 074,264 filed Jul. 16, 1987, U.S. Ser. No. 685,881 filed Apr. 15, 1991, U.S. Ser. No. 574,391 filed Aug. 27, 1990, U.S. Ser. No. 194,024 filed May 13, 1988, and U.S. Ser. No. 074,264 filed Jul. 16, 1987. Each of the above listed patent applications is incorporated herein by reference. Those having ordinary skill in the art can synthesize biologically active peptides based upon reovirus hemagglutinin sigma 1 protein sequences.

Peptides may be conformationally restricted and/or dimerized. In some embodiments, cysteine residues are provided to form disulfide bonds which can cyclicize the peptide or link peptides to form multimers such as dimers. Other means of cyclicizing or dimerizing peptides are well known. For example, cyclization may be accomplished by the "head-tail" method as described in McMurray, J. S. et al. 1993 Int. L. Peptide Protein Res. 42:209–215 and McMurray J. S. and C. A. Lewis 1993 Tetrahedron Letters 34 (50):8059–8062, both of which are incorporated herein by reference. Alternatively, Wood S. J. and R. 1992 Int. J. Peptide Protein Res. 39:533–539, which is incorporated herein by reference, describe cyclization chemistry which may be used to conformationally restrict peptides used in the methods of the present invention.

Conformationally restricted peptides useful in the present invention may be those which bind to the type 3 reovirus receptor and which have been designed as aromatically modified constrained peptides as is referred to in related application U.S. Ser. No. 08/257,783 filed Jun. 10, 1994, which is incorporated herein by reference.

According to the present invention, certain peptides have been identified which are particularly active in the enhancement of epithelial cell proliferation. Some embodiments of the present invention relate to the compounds which are represented by the formula:

$$R_1\text{-}R_2\text{-}R_3\text{-}R_4\text{-}R_5\text{-}R_6\text{-}R_7$$

wherein:

$R_1$ is 1–6 amino acid residues, at least one of which is tyrosine or phenylalanine;

$R_2$ is a linking moiety which bonds to $R_1$, $R_3$ and $R_6$ such that a portion of the molecule is cyclicized;

$R_3$ is 0–13 amino acids;

$R_4$ is 4–6 amino acids;

$R_5$ is 0–13 amino acids;

$R_6$ is a linking moiety which bonds to $R_5$, $R_7$ and $R_2$ such that a portion of the molecule is cyclicized;

$R_7$ is 1–6 amino acid residues, at least one of which is tyrosine or phenylalanine;

wherein: $R_1$, $R_2$, $R_3$, $R_4$, $R_5$, $R_6$ and $R_7$ taken together are made up of 30 amino acids or less;

and $R_4$ is an active sequence having either the formula:

Tyr Ser $R_{41}$ Ser Thr wherein $R_{41}$ is Gly, Pro or a flexible moiety to which bonds to Ser and Ser can be formed and allow them to retain the psi/phi adjustment that occurs when $R_{421}$ is Gly; or the formula:

$R_{42}$ Tyr Ser $R_{41}$ Ser Thr wherein $R_{41}$ is Gly, Pro or a flexible moiety to which bonds to Ser and Ser can be formed and allow them to retain the psi/phi adjustment that occurs when $R_{41}$ is Gly, and $R_{42}$ is Ile, Leu, Val, Gly or Met.

According to some aspects of the invention in which compounds having the above formula are used, $R_1$ is 1–6 amino acid residues, at least one of which is tyrosine or phenylalanine. According to some embodiments, $R_1$ is selected from the group consisting of: Phe-Lys-Thr-Asn-Lys (SEQ ID NO:1); Phe-Lys; Phe-Asn-Lys-Leu (SEQ ID NO:2); Phe; and Tyr. In some embodiments, $R_1$ is Phe or Tyr. In some preferred embodiments, $R_1$ is Phe. It is also contemplated that compounds useful in the methods of the invention have the formula set out above in which $R_1$ is an aromatic moiety, wherein the term "aromatic moiety" is meant to refer to molecular entities which comprise an aromatic group, particularly phenyl groups. It is contemplated that $R_1$ is a phenyl group linked to $R_2$ directly or by some intermediate entity.

According to these aspects of the invention, $R_2$ is a linking moiety. As used herein, the term linking moiety refers to an amino acid residue or other molecular entity which bonds to $R_1$ and $R_6$ to $R_3$ or $R_4$ such that a portion of the molecule is cyclicized. In some embodiments, $R_2$ is an amino acid residue. In some preferred embodiments, $R_2$ is cysteine and linked to a cysteine at $R_6$ by a disulfide bond.

According to the aspects of the invention in which compounds having the above formula are used, $R_3$ is 0–13 amino acids. Generally, $R_3$ residues are used to provide the necessary conformation of the restricted peptides. $R_3$ may also be derived and contribute to the active region of the peptide. In some preferred embodiments, $R_3$ is 1–5 amino acids. In some preferred embodiments, $R_3$ is 1 amino acid. In some preferred embodiments, $R_3$ is 1 amino acid and is selected from the group consisting of: Gly, Val, Ala, Ile or Leu. In some preferred embodiments, $R_3$ is Ile. In some preferred embodiments, $R_3$ is 0 amino acids.

According to the aspects of the invention in which compounds having the above formula are used, $R_4$ is 4–6 amino acids and forms the active region of the molecule. As used herein, the active region refers to the sequence of the peptide that interacts with the receptor. In some embodiments, $R_4$ is either Tyr-Ser-$R_{41}$-Ser-Thr or $R_{42}$ Tyr Ser $R_{41}$ Ser Thr, wherein $R_{41}$ is glycine, proline or a flexible moiety to which bonds to serine and serine can be formed and allow them to retain the psi/phi adjustment that occurs when $R_{41}$ is glycine. According to the invention, $R_{41}$ forms bonds with and connects the serine and serine of $R_4$. The serine and serine residues must retain a psi/phi adjustment similar to that which occurs when $R_{41}$ is glycine. Thus, $R_{41}$ may be glycine, proline or any other moiety in which bonds to the two serines and allows them to retain the psi/phi adjustment that occurs when $R_{41}$ is glycine. In some preferred embodiments, $R_{41}$ is glycine or proline. In preferred embodiments, $R_{41}$ is glycine. In embodiments in which $R_4$ is $R_{42}$-Tyr-Ser-$R_{41}$-Ser-Thr, $R_{42}$ is selected from the group consisting of isoleucine, leucine, valine, glycine and methionine. In preferred embodiments, $R_{42}$ is isoleucine. In preferred embodiments in which $R_4$ is Tyr-Ser-$R_{41}$-Ser-Thr; $R_{41}$ is glycine; that is, $R_4$ is Tyr-Ser-Gly-Ser-Thr (SEQ ID NO:3). In preferred embodiments in which $R_4$ is $R_{42}$-Tyr-Ser-$R_{41}$-Ser-Thr; $R_{41}$ is glycine and $R_{42}$ is isoleucine; that is, $R_4$ is Iso-Tyr-Ser-Gly-Ser-Thr (SEQ ID NO:4).

According to the aspects of the invention in which compounds having the above formula are used, $R_5$ is 0–13 amino acids. Generally, $R_5$ residues are used to provide the necessary conformation of the restricted peptides. $R_5$ may also be derived and contribute to the active region of the peptide. In some preferred embodiments, $R_5$ is 1–5 amino acids. In some preferred embodiments, $R_5$ is 1 amino acid. In some preferred embodiments, $R_5$ is 1 amino acid and is selected from the group consisting of: Gly, Val, Ala, Ile or Leu. In some preferred embodiments, $R_5$ is Ile. In some preferred embodiments, $R_5$ is 0 amino acids.

According to these aspects of the invention, $R_6$ is a linking moiety. As used herein, the term linking moiety refers to an amino acid residue or other molecular entity which bonds to $R_7$ and $R_1$ to $R_4$ or $R_5$ such that a portion of the molecule is cyclicized. In some embodiments, $R_6$ is an amino acid residue. In some preferred embodiments, $R_6$ is cysteine and linked to a cysteine at $R_1$ by a disulfide bond.

According to the aspects of the invention in which compounds having the above formula are used, $R_7$ is 1–6 amino acid residues, at least one of which is tyrosine or phenylalanine. According to some embodiments, $R_7$ is selected from the group consisting of glutamine-phenylalanine, phenylalanine and tyrosine. In some embodiments, $R_7$ is phenylalanine or tyrosine. In some preferred embodiments, $R_7$ is tyrosine. It is also contemplated that compounds useful in the methods of the invention have the formula set out above in which $R_7$ is an aromatic moiety, wherein the term "aromatic moiety" is meant to refer to molecular entities which comprise an aromatic group, particularly phenyl groups. It is contemplated that $R_7$ is a phenyl group linked to $R_6$ directly or by some intermediate entity.

According to one embodiment of the invention, peptides used in a method of the invention are selected form the group consisting of:

Phe-Lys-Thr-Asn-Lys-Cys-Iso-Tyr-Ser-Gly-Ser-Thr-Cys-Gln-Phe (SEQ ID NO:5);

Phe-Lys-Cys-Iso-Tyr-Ser-Gly-Ser-Thr-Cys-Gln-Phe (SEQ ID NO:6);

Phe-Asn-Lys-Leu-Cys-Iso-Tyr-Ser-Gly-Ser-Thr-Cys-Gln-Phe (SEQ ID NO:7);

Phe-Lys-Thr-Asn-Lys-Cys-Iso-Tyr-Ser-Gly-Ser-Thr-Cys-Gln-Phe (SEQ ID NO:8);

Phe-Cys-Iso-Tyr-Ser-Gly-Ser-Thr-Cys-Phe (SEQ ID NO: 9);

and

Phe-Cys-Iso-Tyr-Ser-Gly-Ser-Thr-Cys-Tyr (SEQ ID NO:10).

Peptides can be synthesized by those having ordinary skill in the art using well known techniques and readily available starting materials. According to the invention, references to synthesizing or constructing peptides is herein construed to refer to the production of peptides similar in sequence or structure to the corresponding regions identified by the method of the invention. These peptides may be produced using any method known in the art, including, but not limited to, chemical synthesis as well as biological synthesis in an in vitro or in vivo in a eukaryotic or prokaryotic expression system. In a preferred method, peptides of the invention are produced by solid phase synthesis techniques as taught by Merryfield, (1963) *J. Am. Chem. Soc.*, 15:2149–2154 and J. Stuart and J. D. Young, *Solid Phase Peptide Synthelia*, Pierce Chemical Company, Rockford, Ill. (1984), each of which is incorporated herein by reference.

Peptide mimetics include those molecules which present functional groups responsible for peptide activity but which have non-peptidyl backbones or bonds. Examples of non-peptide molecules which are useful in the methods of the present invention are described in related applications U.S. Ser. No. 674,866 filed Mar. 25, 1991, U.S. Ser. No. 933,013 filed Aug. 20, 1992, now U.S. Pat. No. 5,334,702, and U.S. Ser. No. 08/184,669 filed Jan. 21, 1994, the disclosures of each of which are incorporated herein by reference. Peptide mimetics include compounds that comprise a molecular surface that is substantially similar to the molecular surface which is displayed by peptides of the invention. The compounds bind to the reovirus type 3 receptors on epithelial cells and enhance proliferation of such cells.

The proteins, antibodies, peptides and peptide mimetics of the invention are useful to enhance the proliferation of epithelial cells which have been identified as cells whose proliferation is desirable. The methods of the invention comprise the step of contacting epithelial cells with peptides or peptide mimetics which enhance proliferation.

In the case of diseases, conditions and disorders characterized by insufficient proliferation of epithelial cells, the method of the present invention comprises the step of identifying the individual susceptible to or suffering from diseases, conditions and disorders characterized by insufficient proliferation of epithelial cells, and administering to the individual a therapeutically effective amount of proteins, antibodies, peptides and peptide mimetics which bind to the reovirus hemagglutinin 1 sigma cellular receptor.

Examples of diseases, conditions and disorders characterized by insufficient proliferation of epithelial cells and wounds of tissue that includes proliferating epithelial cell include, but are not limited to, androgenetic alopecia, alopecia areata and telogen effluvium, skin grafting procedures, photoaging, ulcerations, chronic wounds, steroid atrophy, scleroderma psoriasis, ichthyosis, cutaneous T-cell lymphoma, actinic keratoses and seborrheic keratoses, cutaneous ulcers or wounds including those associated with vascular disease (arterial, venous or lymphatic), metabolic disorders (diabetes, necrobiosis lipoidica diabeticorum, porphyria cutanea tarda, gout, pancreatitis), infections (bacterial, viral, fungal), vasculitis (polyarteritis, systemic lupus, rheumatoid, Wegener's granulomatosis, drug-induced), drug side effects (ergotism, halogenodermas, anticoagulant induced necrosis) hematologic abnormalities (hypercoagulable states, sickle cell anemia, thalassemia, polycythemia vera, leukemia, dysproteinemia), tumors (primary cutaneous, metastatic to skin, Kaposi's sarcoma), pyoderma gangrenosum, trauma, burns, pressure sores, neuropathies, insect bites, lichen planus, bullous diseases, and Sweet's syndrome, ocular wounds, corneal transplants and corneal surgery, Herpes keratitis, collagen vascular disease, Sjorgen's syndrome, tear film abnormalities, deinnervation and trauma including alkali burns. Those of ordinary skill in the art can readily identify individuals who are suffering from or susceptible to such diseases, conditions, disorders or wounds including patients undergoing surgical procedures.

The present invention is useful as a method to treat hair loss associated with non-scarring alopecia which includes androgenetic alopecia, alopecia areata and telogen effluvium such as that which occurs secondary to medications, hormonal abnormalities, febrile illness, pregnancy, stress or other factors. Individuals susceptible to or suffering from androgenetic alopecia, alopecia areata or telogen effluvium can be readily identified. Physicians can readily and routinely diagnose those patients suffering from these conditions. Furthermore, individuals with genetic predisposition and susceptibility to certain hair loss conditions can be identified. Those of ordinary skill in the art can therefore identify individuals susceptible to or suffering from androgenetic alopecia, alopecia areata or telogen effluvium.

Once an individual susceptible to or suffering from androgenetic alopecia, alopecia areata or telogen effluvium has been identified, compounds according to the invention may be administered to reduce the severity of the hair loss and/or promote regrowth of hair.

In the case of treating wounds of tissue that includes proliferating epithelial cells, the method of the present invention comprises the step of identifying the individual susceptible to or suffering from wounds of tissue that includes proliferating epithelial cells, and administering to the individual a therapeutically effective amount of a compound according to the invention. Physicians can readily diagnose those patients suffering from wounds and injuries involving epithelial cells. Once an individual with a wound or injury involving epithelial cells has been identified, compounds according to the invention may be administered to reduce the severity of scarring and to accelerate regrowth of tissue. The enhancement of epithelial regrowth reduces the risk of infection and complications associated therewith.

Methods of the present invention comprise administering a single or multiple doses of the compounds of the invention. Preferred for human pharmaceutical use are pharmaceutical compositions that comprise the compounds of the present invention in combination with a pharmaceutically acceptable carrier or diluent.

The pharmaceutical compositions of the present invention may be administered by any means that enables the active agent to reach the agent's site of action in the body of a mammal. In the case of the peptides of the invention, the primary focus is the ability to reach and bind with reovirus hemagglutinin 1 sigma cellular receptor. Because proteins are subject to being digested when administered orally, parenteral administration, i.e., intravenous, subcutaneous, intramuscular, would ordinarily be used to optimize absorption. In some preferred embodiments, pharmaceutical compositions which comprise the compounds of the present invention are administered topically or as a lavage.

Pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

For parenteral administration, the compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field.

For example, a parenteral composition suitable for administration by injection is prepared by dissolving 1.5% by weight of active ingredient in 0.9% sodium chloride solution.

According to the present invention, the compound may be administered to tissue of an individual topically or by lavage. The compounds may be formulated as a cream, ointment, salve, douche, suppository or solution for topical administration or irrigation. Formulations for such routes administration of pharmaceutical compositions are well known.

Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations according to the present invention are preferably provided sterile and pyrogen free.

One of skill in the art of pharmaceutical formulations, e.g., having an advanced degree in Pharmaceutics or Pharmaceutical Sciences, can prepare a variety of appropriate dosage forms and formulations for the compositions of the invention with no more than routine experimentation. A number of texts in the field, a,g., *Remington's Pharmaceutical Sciences* and *The U.S. Pharmacopoeia/National Formulary*, latest editions, provide considerable guidance in this respect.

A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

In addition to the usual considerations of stability and bioavailability, in order to achieve adequate mucosal immunity, the dosage form will provide adequate physical and temporal contact with the selected mucosa. The active ingredients) can be formulated as a single phase or two-phase system, and in liquid, solid or semisolid dosage form, for example, cream, gel, emulsion, suspension, ointment, suppository, tablet. The formulation vehicle may be aqueous, oleaginous, or an oil-in-water or water-in-oil emulsion, preferably water/oil. The active ingredients may be formulated in sterile water or saline.

---

We claim:

1. A method of enhancing proliferation of an epithelial cell of the skin, comprising contacting the epithelial cell of the skin with a compound that binds to a reovirus type 3 receptor, and enhancing proliferation of said cell.

2. The method of claim 1 in which the compound is an antibody or an antigen-binding fragment thereof.

3. The method of claim 2 in which the antibody is a monoclonal antibody.

4. The method of claim 2 in which the antibody is a chimeric antibody.

5. The method of claim 2 in which the antibody is a humanized antibody.

6. The method of claim 1 in which the compound is a reovirus hemagglutinin sigma 1 protein or a receptor-binding fragment thereof.

7. The method of claim 1 in which the compound is a peptide.

8. The method of claim 7 in which the peptide has the formula:

$R_1$-$R_2$-$R_3$-$R_4$-$R_5$-$R_6$-$R_7$ wherein:

$R_1$ is an aromatic moiety;

$R_2$ is a linking moiety which forms a bond with $R_1$, $R_3$ and $R_6$;

$R_3$ is 0 amino acid;

$R_4$ has the formula of $R_{42}$-Tyr-Ser-$R_{41}$-Ser-Thr wherein $R_{41}$ is Gly or Pro and $R_{42}$ is Ile, Leu, Val, Gly, Met or absent;

$R_5$ is 0 amino acid;

$R_6$ is a linking moiety which forms a bond with $R_2$, $R_5$ and $R_7$; and $R_7$ is an aromatic moiety.

9. The method of claim 8 in which $R_1$ contains at least one Phe or Tyr, $R_2$ and $R_6$ are Cys, $R_{41}$ is Gly, $R_{42}$ is Ile and $R_7$ contains at least one Phe or Tyr.

10. The method of claim 9 in which the peptide is selected from the group consisting of: SEQ ID NO:5, SEQ ID NO:6, SEQ ID NO:7, SEQ ID NO:8, SEQ ID NO:9 and SEQ ID NO:10.

11. The method of claim 1 in which the compound is a peptide mimetic.

12. A method of treating an individual in need of epithelial cell proliferation of the skin, comprising topically administering to the individual a therapeutically effective amount of a compound that binds to a reovirus type 3 receptor, and enhancing epithelial cell proliferation of the skin in the individual.

13. The method of claim 12 in which the compound is an antibody or an antigen-binding fragment thereof.

14. The method of claim 13 in which the antibody is a monoclonal antibody.

15. The method of claim 13 in which the antibody is a chimeric antibody.

16. The method of claim 13 in which the antibody is a humanized antibody.

17. The method of claim 12 in which the compound is a reovirus hemagglutinin sigma 1 protein or a receptor-binding fragment thereof.

18. The method of claim 12 in which the compound is a peptide.

19. The method of claim 18 in which the peptide has the formula:

$R_1$-$R_2$-$R_3$-$R_4$-$R_5$-$R_6$-$R_7$ wherein:

$R_1$ is an aromatic moiety;

$R_2$ is a linking moiety which forms a bond with $R_1$, $R_3$ and $R_6$;

$R_3$ is 0 amino acid;

$R_4$ has the formula of $R_{42}$-Tyr-Ser-$R_{41}$-Ser-Thr wherein $R_{41}$ is Gly or Pro and $R_{42}$ is Ile, Leu, Val, Gly, Met or absent;

$R_5$ is 0 amino acid;

$R_6$ is a linking moiety which forms a bond with $R_2$, $R_5$ and $R_7$; and $R_7$ is an aromatic moiety.

20. The method of claim 19 in which $R_1$ contains at least one Phe or Tyr, $R_2$ and $R_6$ are Cys, $R_{41}$ is Gly, $R_{42}$ is Ile and $R_7$ contains at least one Phe or Tyr.

21. The method of claim 20 in which the peptide is selected from the group consisting of: SEQ ID NO:5, SEQ ID NO:6, SEQ ID NO:7, SEQ ID NO:8, SEQ ID NO:9 and SEQ ID NO:10.

22. The method of claim 12 in which the compound is a peptide mimetic.

23. The method of claim 12 in which the individual suffers from psoriasis, burns, wounds or ulcers of the skin.

24. A method of enhancing ocular epithelial cell proliferation, comprising contacting an ocular epithelial cell with a compound that binds to a reovirus type 3 receptor, and enhancing proliferation of said cell.

25. The method of claim 24 in which the compound is an antibody or an antigen-binding fragment thereof.

26. The method of claim 25 in which the antibody is a monoclonal antibody.

27. The method of claim 25 in which the antibody is a chimeric antibody.

28. The method of claim 25 in which the antibody is a humanized antibody.

29. The method of claim 24 in which the compound is a reovirus hemagglutinin sigma 1 protein or a receptor-binding fragment thereof.

30. The method of claim 24 in which the compound is a peptide.

31. The method of claim 30 in which the peptide has the formula:

$R_1$-$R_2$-$R_3$-$R_4$-$R_5$-$R_6$-$R_7$ wherein:

$R_1$ is an aromatic moiety;

$R_2$ is a linking moiety which forms a bond with $R_1$, $R_3$ and $R_6$;

$R_3$ is 0 amino acid;

$R_4$ has the formula of $R_{42}$-Tyr-Ser-$R_{41}$-Ser-Thr wherein $R_{41}$ is Gly or Pro and $R_{42}$ is Ile, Leu, Val, Gly, Met or absent;

$R_5$ is 0 amino acid;

$R_6$ is a linking moiety which forms a bond with $R_2$, $R_5$ and $R_7$; and $R_7$ is an aromatic moiety.

32. The method of claim 31 in which $R_1$ contains at least one Phe or Tyr, $R_2$ and $R_6$ are Cys, $R_{41}$ is Gly, $R_{42}$ is Ile and $R_7$ contains at least one Phe or Tyr.

33. The method of claim 32 in which the peptide is selected from the group consisting of: SEQ ID NO:5, SEQ ID NO:6, SEQ ID NO:7, SEQ ID NO:8, SEQ ID NO:9 and SEQ ID NO:10.

34. The method of claim 24 in which the compound is a peptide mimetic.

35. A method of treating an individual in need of ocular epithelial cell proliferation, comprising topically administering to the individual a therapeutically effective amount of a compound that binds to a reovirus type 3 receptor, and enhancing ocular epithelial cell proliferation in the individual.

36. The method of claim 35 in which the compound is an antibody or an antigen-binding fragment thereof.

37. The method of claim 36 in which the antibody is a monoclonal antibody.

38. The method of claim 36 in which the antibody is a chimeric antibody.

39. The method of claim 36 in which the antibody is a humanized antibody.

40. The method of claim 35 in which the compound is a reovirus hemagglutinin sigma 1 protein or a receptor-binding fragment thereof.

41. The method of claim 35 in which the compound is a peptide.

42. The method of claim 41 in which the peptide has the formula:

$R_1$-$R_2$-$R_3$-$R_4$-$R_5$-$R_6$-$R_7$ wherein:

$R_1$ is an aromatic moiety;

$R_2$ is a linking moiety which forms a bond with $R_1$, $R_3$ and $R_6$;

$R_3$ is 0 amino acid;

$R_4$ has the formula of $R_{42}$-Tyr-Ser-$R_{41}$-Ser-Thr wherein $R_{41}$ is Gly or Pro and $R_{42}$ is Ile, Leu, Val, Gly, Met or absent;

$R_5$ is 0 amino acid;

$R_6$ is a linking moiety which forms a bond with $R_2$, $R_5$ and $R_7$; and $R_7$ is an aromatic moiety.

43. The method of claim 42 in which $R_1$ contains at least one Phe or Tyr, $R_2$ and $R_6$ are Cys, $R_{41}$ is Gly, $R_{42}$ is Ile and $R_7$ contain at least one Phe or Tyr.

44. The method of claim 43 in which the peptide is selected from the group consisting of: SEQ ID NO:5, SEQ ID NO:6, SEQ ID NO:7, SEQ ID NO:8, SEQ ID NO:9 and SEQ ID NO:10.

45. The method of claim 35 in which the compound is a peptide mimetic.

46. The method of claim 35 in which the individual suffers from ocular burns, wounds or ulcers.

* * * * *